United States Patent [19]
Feldman

[11] Patent Number: 5,453,009
[45] Date of Patent: Sep. 26, 1995

[54] METHOD OF AND SYSTEM FOR DENTAL TREATMENT

[76] Inventor: Yasha Feldman, 3029 Brighton 12 St., #C-7, Brooklyn, N.Y. 11235

[21] Appl. No.: 175,225

[22] Filed: Dec. 29, 1993

[51] Int. Cl.$^6$ .............. A61C 5/00; A61C 1/00; A61C 3/00; A61C 1/02
[52] U.S. Cl. .............. 433/215; 433/27; 433/99
[58] Field of Search .............. 433/27, 28, 98, 433/99, 215, 223, 229; 128/898

[56] References Cited

U.S. PATENT DOCUMENTS

| | | | |
|---|---|---|---|
| 4,014,097 | 3/1977 | Pameijer | 433/27 |
| 4,478,580 | 10/1984 | Barrut | 433/223 |
| 4,564,355 | 1/1986 | Traiger et al. | 433/215 |
| 4,571,681 | 2/1986 | Beier et al. | 433/101 X |
| 4,575,805 | 3/1986 | Moermann et al. | 433/223 X |
| 4,818,227 | 4/1989 | Krueger | 433/27 |
| 4,889,422 | 12/1989 | Pavlidis | 128/898 X |
| 4,964,770 | 10/1990 | Steinbichler et al. | 433/223 |
| 5,025,785 | 6/1991 | Weiss | 128/898 X |
| 5,224,049 | 6/1993 | Mushabac | 433/223 X |
| 5,234,404 | 8/1993 | Tuttle et al. | 128/898 X |

Primary Examiner—Nicholas D. Lucchesi
Attorney, Agent, or Firm—Ilya Zborovsky

[57] ABSTRACT

A dental treatment is performed in accordance with examination of a patient and determination of a required sequence of treatments by a computer, based on the examination results.

7 Claims, 1 Drawing Sheet

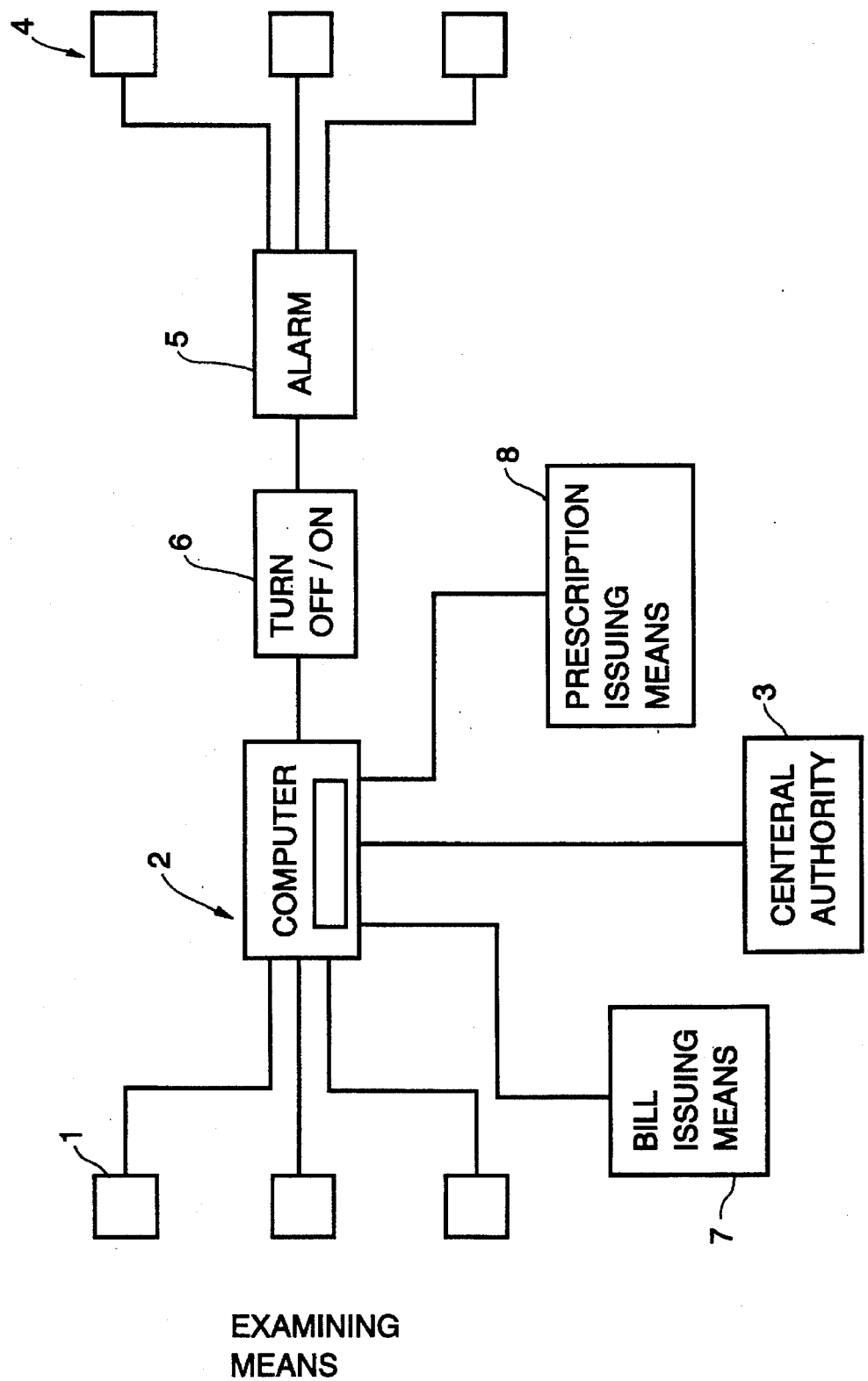

METHOD OF AND SYSTEM FOR DENTAL TREATMENT

BACKGROUND OF THE INVENTION

The present invention relates to a method of and a system for dental treatment.

In dental treatment dentists usually determine the condition of a patient's mouth and types of treatments which in their opinion must be performed in a certain sequence. In some instances dentists who are still not experienced can select an incorrect sequence of treatment and perform treatments which can be performed at a later time while really emergency treatment are postponed. In some rare instances dentists select first those treatments which are more profitable and not those which are really necessary at that very moment. Sometimes even unnecesary treatments are performed for purely commercial purposes. It is believed to be clear that it is advisable to develop a method and a system which are superior with respect to existing methods and systems.

SUMMARY OF THE INVENTION

Accordingly, it is an object of the present invention to provide a new method of and system for detntal treatment, which avoid the disadvantages of the prior art.

In keeping with these objects and with others which will become apparent hereinafter, one feature of the present invention resides, briefly stated, in a method if dental treatment, in accordance with which dental conditions of a patient are monitored, introduced into a computer, compared with a list of dental conditions stored, and then a sequence of required treatment is determined. In addition, dental instruments are also connected with the computer, and if a dental instrument is used not in accordance with the determined sequence, a warning signal is produced, and also the instrument can be turned on. Finally, the computer produced prescription for medications, and also bills for services provided.

In accordance with another feature of the present invention, a system is provided which comprises dental condition evaluating means, computer means for comparing the evaluated dental conditions with a list of conditions to determine a required sequence, dental instruments connected with the computer to perform dental treatments in accordance with the determined sequence, means producing a warning signal when the sequence is not followed, means for turning off the dental instruments when the desired sequence is followed, and means for producing bills for services.

The novel features of the present invention are set forth in the appended claims. The invention itself, however, both as to its construction and its manner will be best understood from the following description of preferred embodiments which is accompanied by the following drawings, in which the method and the system of the present invention are schematically illustrated.

BRIEF DESCRIPTION OF THE DRAWINGS

The single FIGURE of the drawings is a view schematically illustrating a new method of and a system for performing dental treatment in accordance with the present invention.

DESCRIPTION OF PREFERRED EMBODIMENTS

In accordance with the present invention when a patient comes to a dentist for dental treatment, the dentist uses examining means which is identified as a whole with reference numeral 1 in the drawings. The examining means can include a plurality of sensors, scanning elements, X-ray taking elements, etc., with which the dentist examines all parts of the patient's mouth.

The examining means 1 are connected with data processing means which can be formed as a computer 2. The computer has a memory which stores information of all possible dental diseases and problems, and based on the information received from the examining means 1, determines the gravity of all diseases and problems of the examined patient, and based on this determination determines a sequence of treatments which is required for this particular patient. This sequence can be displayed on a display of the computer so that both the patient and the dentist can see it, and the patient can be sure that the dentist will follow the determined sequence. It is also possible to send the information to a central authority, for example dental insurance company 3 for verification purposes.

When the required sequence of treatments is determined, the dentist uses dental instruments 4 for performing dental treatment in accordance with the determined sequence. If he does not use the dental instruments exactly in accordance with the determined sequence, a warning signal is produced by a warning device 5 and alarm can be triggered. For example, if the computer determine that before treating a gum disease it is necessary to do a root canal and then to treat just one tooth completely, but the dentist starts nevertheless with the treatment of the gum disease, a warning signal will be produced. All dental instruments which are used not in accordance with a desired determined sequence can be turned off by activating means 6.

The computer 2 also has means 7 for issuing prescriptions and means 8 for issuing bills for services performed. Thus, there can be no mistakes in presribing respective medications or overcharging patients. The whole process of treatment can be performed based on accurate determination of the required treatment steps by the computerised system so that dentists cannot make mistakes, the process is also monitored by the patients, and finally verified by a respective authority, for example dental insurance company, or government agency (MEDICAID, MEDICARE, etc).

The computer can also moniter the time of treatment.

The subject matter of the invention is described above, but the invention is not limited to the details shown. What is desired to be protected by letters patent is set forth in the claims.

I claim:

1. A method of dental treatment, comprising the steps of examining a patient to determine a plurality of dental conditions to be treated;

storing in a computer all possible dental conditions and all possible sequences of their treatments;

determining by the computer a required sequence of treatment of said dental conditions based on said stored sequences;

performing the treatments in accordance with the required sequence with dental instruments;

issuing a warning signal when the treatments with the dental instruments are not performed in accordance with the determined sequence; and turning off a dental instrument which is not used in accordance with the determined sequence.

2. A method as defined in claim 1; and further comprising the step of prescribing medications for the determined treatments by said computer.

3. A method as defined in claim 1; and further comprising means for producing bills in accordance with said treatments, connected with said computer.

4. A system for dental treatment, comprising means for examining a patient to determine a plurality of dental conditions to be treated;

computer means storing substantially all possible dental conditions and sequences of their treatments, said computer means being connected with said examining means and determining a required sequence of treatment of said determined dental conditions based on said stored sequences;

means for performing treatment of said dental conditions in accordance with the determined sequence of treatments, said means for performing treatment including a plurality of dental instruments;

means for issuing a warning signal when the treatments with the dental instruments are not performed in accordance with the determined sequence; and means for turning off a dental instrument which is used to perform a dental treatment not in accordance with the determined sequence.

5. A system as defined in claim 4; and further comprising means connected with said computer for prescribing medications in accordance with the determined dental conditions.

6. A system as defined in claim 4; and further comprising means connected with the computer for producing bills in accordance with the performed dental treatments.

7. A system for dental treatment, comprising means for examining a patient to determine a plurality of dental conditions to be treated;

computer means storing substantially all possible dental conditions and sequences of their treatments, said computer means being connected with said examining means and determining a required sequence of treatment of said determined dental conditions based on said stored sequences;

means for performing treatment of said dental conditions in accordance with the determined sequence of treatments, said means for performing treatment including a plurality of dental instruments:

means for issuing a warning signal when the treatments with the dental instruments are not performed in accordance with the determined sequence:

means for turning off a dental instrument which is used to perform a dental treatment not in accordance with the determined sequence;

means for prescribing medications in accordance with dental conditions determined by said examining means; and means for producing bills in accordance with the treatment performed by said means for performing treatment.

* * * * *